(12) United States Patent
Griffin

(10) Patent No.: US 9,321,095 B2
(45) Date of Patent: Apr. 26, 2016

(54) APPARATUSES AND METHODS FOR CUTTING POROUS SUBSTRATES

(75) Inventor: Weston Blaine Griffin, Niskayuna, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 198 days.

(21) Appl. No.: 12/826,877

(22) Filed: Jun. 30, 2010

(65) Prior Publication Data

US 2012/0000330 A1  Jan. 5, 2012

(51) Int. Cl.
*B21D 45/08* (2006.01)
*B21D 45/00* (2006.01)
*B26D 7/02* (2006.01)
*B26F 1/02* (2006.01)
*G01N 1/28* (2006.01)
*B26F 1/14* (2006.01)

(52) U.S. Cl.
CPC .............. *B21D 45/006* (2013.01); *B21D 45/08* (2013.01); *B26D 7/02* (2013.01); *B26F 1/02* (2013.01); *G01N 1/286* (2013.01); *B26F 1/14* (2013.01); *G01N 2001/288* (2013.01); *Y10T 83/2159* (2015.04)

(58) Field of Classification Search
USPC .......................................... 83/686, 140, 143
IPC .......... B21D 45/0006,45/08; B26F 1/14; Y10T 83/2159
See application file for complete search history.

(56) References Cited

U.S. PATENT DOCUMENTS

| 2,217,393 | A | * | 10/1940 | Webb | ............................... | 30/241 |
| 2,225,342 | A | * | 12/1940 | Hyatt | ............................... | 83/136 |
| 2,953,051 | A |   | 9/1960  | Grossman | | |
| 3,079,824 | A | * | 3/1963  | Schott | ............................ | 83/140 |
| 3,114,280 | A | * | 12/1963 | Schott | ............................ | 83/140 |
| 3,205,742 | A | * | 9/1965  | Williamson | .................... | 83/140 |
| 3,357,755 | A | * | 12/1967 | Danly | ............................ | 384/49 |
| 3,722,337 | A | * | 3/1973  | Brolund et al. | ................. | 83/137 |
| 3,779,113 | A | * | 12/1973 | Jestin | ............................. | 83/140 |
| 3,935,772 | A | * | 2/1976  | Demus et al. | .................. | 83/140 |
| 4,341,735 | A |   | 7/1982  | Seifried | | |
| 4,457,196 | A | * | 7/1984  | Cady | ............................... | 83/140 |
| 4,489,053 | A |   | 12/1984 | Azuma et al. | | |
| 4,993,295 | A | * | 2/1991  | Dacey, Jr. | ........................ | 83/140 |
| 5,045,302 | A |   | 9/1991  | Kelly et al. | | |
| 5,081,891 | A | * | 1/1992  | Johnson et al. | ................. | 83/140 |

(Continued)

FOREIGN PATENT DOCUMENTS

CN  1331081 A  1/2002
CN  101614628 A  12/2009

(Continued)

OTHER PUBLICATIONS

EP Office Action from corresponding EP Application No. 11743785.5 dated Nov. 27, 2013.

(Continued)

*Primary Examiner* — Kenneth E Peterson
(74) *Attorney, Agent, or Firm* — Fletcher Yoder, P.C.

(57) ABSTRACT

Apparatuses and methods for cutting a sample piece, having a shape and an outer dimension, out of a porous substrate, comprising: a puncher having an outermost dimension at a punch head; a stripping sleeve; a die having an innermost dimension that is larger than the outermost dimension of the punch head; and a fixture that holds the die in a fixed position relative to the puncher and stripping sleeve.

10 Claims, 9 Drawing Sheets

(56) References Cited

U.S. PATENT DOCUMENTS

| | | | |
|---|---|---|---|
| 5,176,057 A * | 1/1993 | Chun et al. | 83/139 |
| 5,300,280 A | 4/1994 | Derosch et al. | |
| 5,460,057 A | 10/1995 | Ostrup | |
| 5,638,170 A | 6/1997 | Trinka et al. | |
| 6,342,143 B1 | 1/2002 | Minden | |
| 6,372,504 B1 | 4/2002 | Tervamaki et al. | |
| 6,713,042 B2 | 3/2004 | Liu | |
| 7,029,653 B1 | 4/2006 | Kawai et al. | |
| 7,052,672 B2 | 5/2006 | Forster et al. | |
| 7,954,404 B2 * | 6/2011 | Thielges et al. | 83/140 |
| 2005/0129579 A1 | 6/2005 | Morrison | |
| 2006/0216781 A1 | 9/2006 | Gebing | |
| 2006/0246419 A1 | 11/2006 | Thornton et al. | |
| 2008/0105095 A1 | 5/2008 | Ekman et al. | |
| 2011/0132111 A1 | 6/2011 | Shoemaker et al. | |

FOREIGN PATENT DOCUMENTS

| | | | |
|---|---|---|---|
| DE | 10048643 A1 | | 5/2001 |
| DE | 20022666 U1 | | 1/2002 |
| FR | 1053907 | * | 10/1953 |
| WO | 2006094388 A1 | | 9/2006 |
| WO | 2009115852 A2 | | 9/2009 |
| WO | 2010043668 A1 | | 4/2010 |

OTHER PUBLICATIONS

PCT Search Report and Written Opinion from corresponding PCT Application No. PCT/EP2011/060853 dated Sep. 23, 2011.

GB Office Action from corresponding GB Application No. 1222224.6 dated Mar. 31, 2014.

Tanno et al., "Radiopharmaceuticals", Medicine and Drug, vol. No. 30, pp. 268, 1994.

Chinese Office Action issued in connection with corresponding CN Application No. 201180032550.6 on Aug. 29, 2014.

European Office Action issued in connection with corresponding EP Application No. 11743785.5 on Oct. 8, 2015.

* cited by examiner

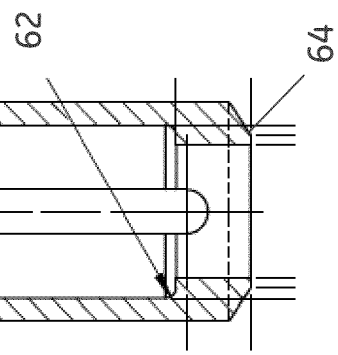
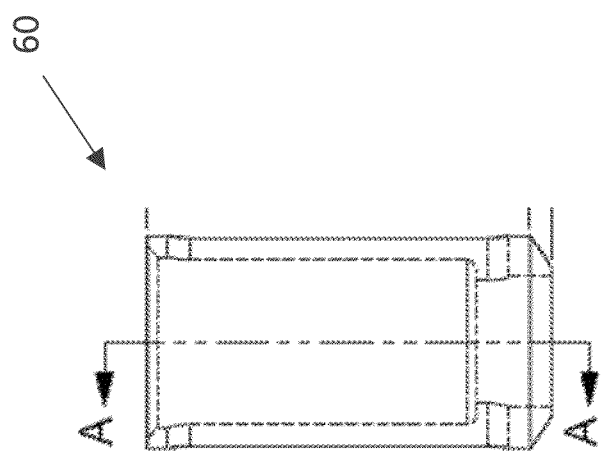
FIG. 5B
FIG. 5A

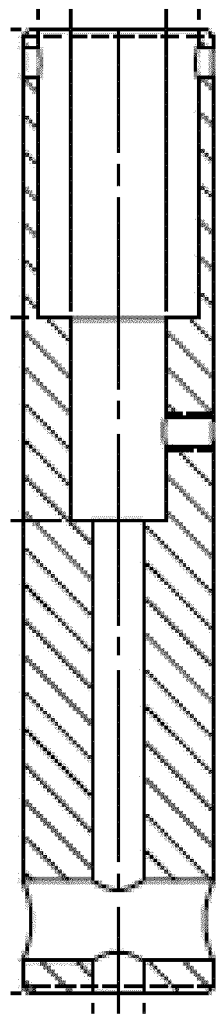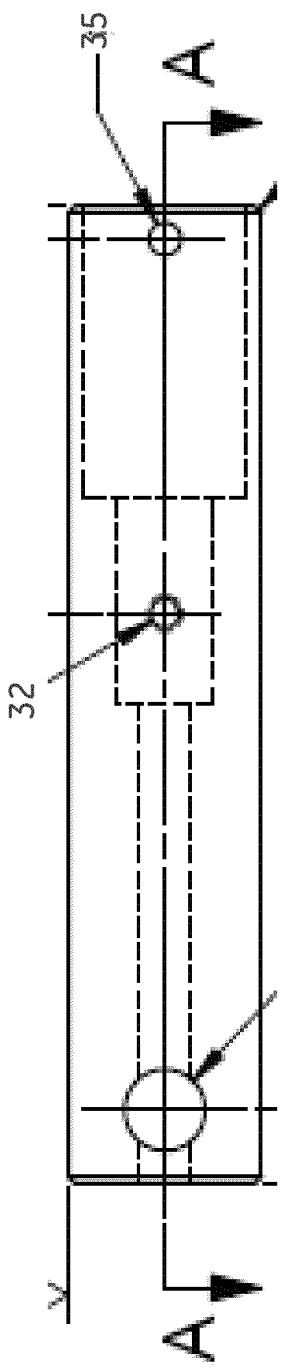

APPARATUSES AND METHODS FOR CUTTING POROUS SUBSTRATES

BACKGROUND

The invention relates generally to apparatuses and methods for cutting porous substrates.

Porous substrates, such as cellulose matrices (e.g. 31 ETF, FTA and FTA elute cards available from Whatman) are often used to store biological samples, such as blood. A new application area for these cards is in the pharmaceutical industry, which is using them to store dried blood samples from pharmacokinetic and toxicokinetic studies. When it is time to analyze the amount of drug or drug metabolite in the dried blood spot, the current methods require the user to cut the sample out of the card, usually a 1-6 mm diameter circle, place the cut disc in a vial or well with extraction fluid, and then shake/vortex for a set period of time. The extraction fluid is then removed and analyzed using a method such as LC-MS.

The pharmaceutical industry is expecting to process a large number of samples per day and is therefore looking for ways to automate the process. However, unlike typical blanking or punching operations, the stock material used in such processes is not fed from a roll-to-roll system. The FTA cards typically contain 1-4 samples locations and thus must be handled individually, even when high-throughput processing is required. Additionally, the desired punch location can vary from card to card. Thus, the cards are typically manipulated and positioned by a robotic end effector or mechanism to move the cards to the correct location with respect to the punch. To allow for high-density card storage, the card gripper fingers should be as thin as possible. However, very thin gripper fingers are unlikely able to prevent the punch retraction forces from moving or pulling the card from the gripping system. Thus the integration of a stripping sleeve with the punch prevents motion of the paper. Additionally, as a variety of card types exist, the stripping sleeve is essentially independent of the desired card type to be punched.

One approach to preventing card motion during punching or retraction is to create a stiff gripper that substantially encompasses the perimeter of the FTA card and prevent the card from being pulled up/out during the retraction process. However, the design limits the storage density of the cards and must be custom designed for each new card shape.

Another problem associated with automated the sample processes systems that comprise disc cutting and extraction is that the tiny discs are highly prone to the effects of static electricity or even a light breeze. There are numerous reports of cut discs being lost during the cutting step or during transport of the cut discs. Currently, sample discs are lost due to factors such as static electricity and air movement. For example, static charges may build up in the plastic multiwall plates or tubes, causing the discs to sticks to the plates or tubes walls. The discs sometimes stick to the punching device, or, later in the process, the discs sometimes stick to the liquid handling probes, which, when the probes are withdrawn from the well, the discs are inadvertently removed from the well. The current instruments on the market focus on reducing sample disc loss by reducing the amount of air movement in the system (enclosed system) and adding anti-static devices (such as humidifiers).

BRIEF DESCRIPTION

The apparatuses and methods of the invention generally comprise an integrated stripping sleeve, which greatly simplifies the design of the card gripping system and eliminates the need for additional actuators to hold the card in place during the blanking operation. Additionally, the components of the apparatuses that are most prone to wear are easily replaced making the apparatuses field serviceable and user friendly. The apparatus also does not require an ejector pin, unlike current punching devices, to push a disc through the die and into the sample receptacle such as a well plate. The apparatuses comprise various features that alone, or in combination, also work to ensure that a sample piece is cut cleanly out of the porous substrate and is not drawn back up into the apparatus when the puncher is retracted or otherwise misplaced during the cutting operation.

An embodiment of an apparatus of the invention, for cutting a sample piece, having a shape and an outer dimension, out of a porous substrate, generally comprises: a puncher having an outermost dimension at a punch head; a stripping sleeve; a die having an innermost dimension that is larger than the outermost dimension of the punch head; and a fixture that holds the die in a fixed position relative to the puncher and stripping sleeve. The stripping sleeve in one or more of the embodiments is spring loaded. The apparatus may also comprise one or more guides, wherein a pillar comprises a seat for the guides and the stripping sleeve comprises one or more slots or channels that engage the guides. In another embodiment, the pillar comprises the channels and the stripping sleeve comprises the seat for the guides The fixture may comprise the pillar, in which the puncher is seated. In some of the embodiments, the components of the apparatus, such as but not limited to, the pillar and puncher are removeable from the fixture by disengaging the engaging components. The apparatus may further comprise a ball bearing cage through which the pillar can move and may comprise a roller sleeve that supports the cage.

In one or more of the embodiments, the fixture is a c-frame having an upper arm that supports the roller sleeve and a lower arm that supports the die. The apparatus may comprise sleeve guides and one or more channels that engage the guides. In at least one embodiment, wherein the pillar comprises a seat for the guide, and the stripping sleeve comprises one or more channels that engage the guides. In another embodiment, the sleeve comprises a seat for the guide and the pillar comprises the channels that engage the guides.

In some embodiments, the punch head has a length and the channels have a length that corresponds to the punch head length, or is substantially the same length as the die length. The die may have an upper end and a lower end and an inner diameter that is larger on the lower end than an inner diameter on the upper end. In some embodiments, the inner diameter of the die increases gradually from the upper end to the lower end.

In one or more of the embodiments, the puncher is coaxially located within the sleeve and the puncher has a path axis along which the punch moves within the sleeve. The sleeve may be spring-loaded and has a shoulder against which the spring presses. The spring may be coaxially located between an inner surface of the sleeve and an outer surface of the puncher.

The fixture may comprise a pillar, in which the puncher is seated, and may further comprise a ball bearing cage through which the pillar can move and a roller sleeve that supports the cage.

An example of a method of the invention, for punching out pieces of a porous substrate, generally comprises: loading the porous substrate onto a support comprising a die; actuating a puncher, having a punch head, and a stripping sleeve so that the sleeve holds the porous substrate against the support as the punch head passes through the die to cut a piece from the porous substrate and push the piece through the die into a receptacle; and the sleeve holds the porous substrate against the support as the punch head is retracted through the die and substrate; and retracting the punch head and then the stripping sleeve. In some methods, the punched piece comprises a biological sample.

The receptacle may comprise a well on a multi-well plate. The receptacles may also comprise one or more vials seated, for example, on a handling system.

DRAWINGS

These and other features, aspects, and advantages of the present invention will become better understood when the following detailed description is read with reference to the accompanying drawings in which like characters represent like parts throughout the drawings, wherein:

FIG. 5A is a side view of another embodiment of the stripping sleeve with the inner wall shown in phantom and FIG. 5B is a cross-sectional view of the stripping sleeve shown in FIG. 5A through line A-A;

Figure 10C:
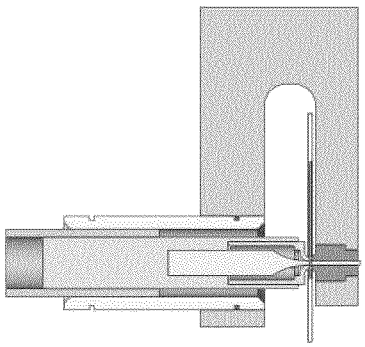
Figure 10B:
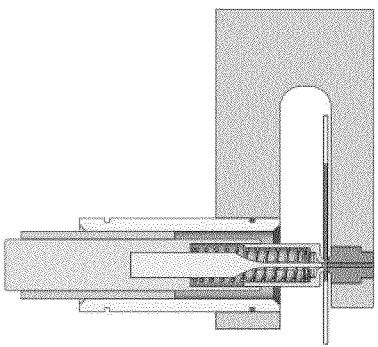
Figure 10A:
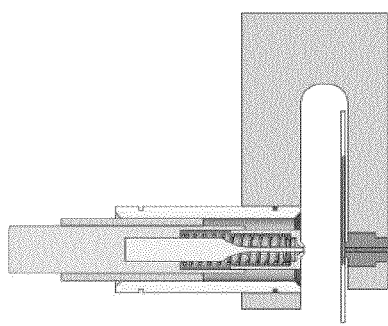

FIG. 9A is a side view of an embodiment of the pillar and FIG. 9B is a cross-sectional view of the embodiment shown in FIG. 9A through line A-A; and FIGS. 10A-10C show an embodiment of the apparatus in progressive stages of action. FIG. 10A is a cross-sectional view of an embodiment of the apparatus with a porous substrate on the support, FIG. 10B is the apparatus with the stripper sleeve and puncher deployed and in contact with the card, and FIG. 10C shows the puncher fully extended after cutting a piece from the card and pushing it through the die of the punching bushing.

DETAILED DESCRIPTION

The methods and apparatuses of the invention are in part adapted to prevent the loss of samples located on porous substrates, such as FTA paper, when processing the samples, such as dried blood spots. These methods and apparatuses may be incorporated into systems designed, for example, to automate the cutting of discs from dried samples on carrier substrates such as cellulose matrices or polymer membranes.

For example, during the preparation of some samples, such as dried blood spots on cellulose cards, a small punch (e.g. 1-6 mm in diameter) is cut out and placed into a wellplate or tube for subsequent processing. One or more of the embodiments of the methods and apparatuses comprises a spring-loaded stripping sleeve that holds the porous substrate against a support while a puncher punches a piece out of the porous substrate, through a die and into a receptacle and while the puncher is retracted from the subsequent hole in the porous substrate.

Figure 1:
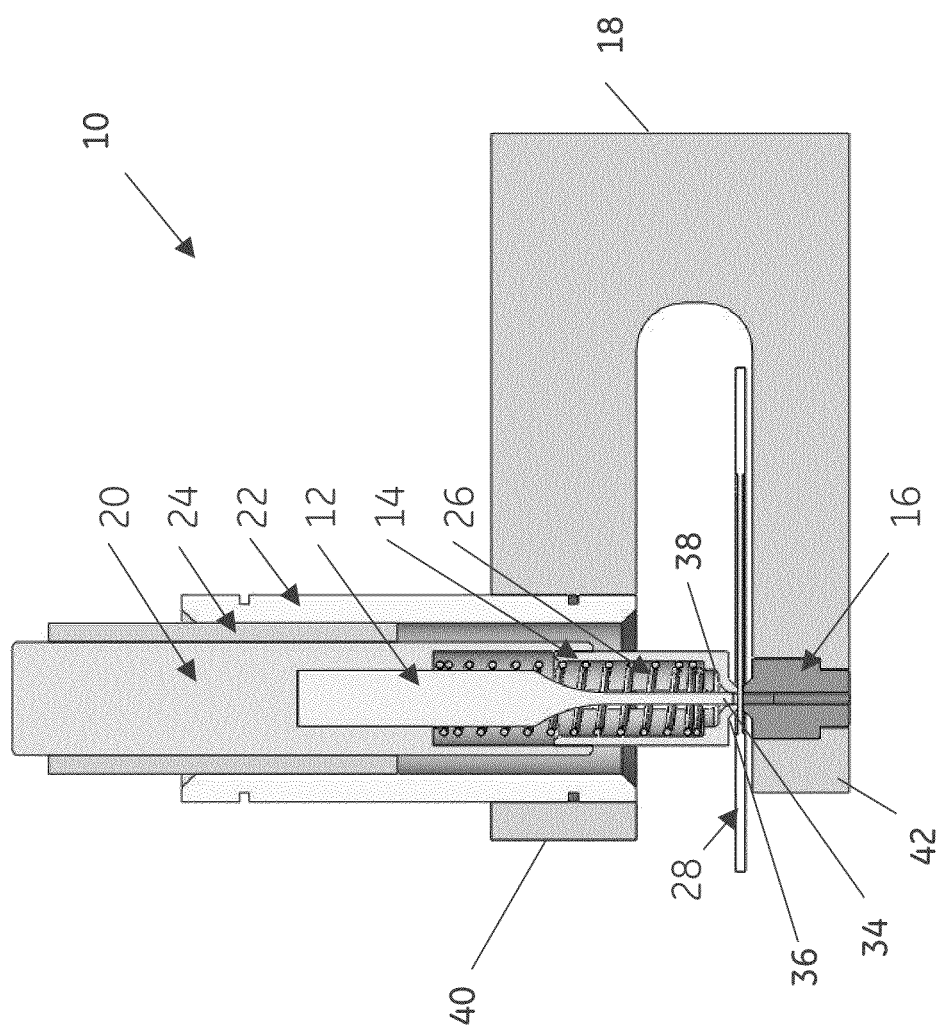
FIG. 1 is a cross-sectional side view of an embodiment of the apparatus of the invention.

An embodiment of the apparatus of the invention is generally shown and referred to in FIG. 1 as apparatus 10. Apparatus 10 comprises punch 12 having a punch head 34, stripping sleeve 14, pillar 20 in which punch 12 is seated, a hard-liner support 22 which is fixed to C-frame support 18, and die 16 which is seated in the lower arm of C-frame support 18. Stripping sleeve 14 is spring loaded by load spring 26 which surrounds punch 12 and is also seated in pillar 20 and actuates stripping sleeve 14 by pressing against shoulder 38 of stripping sleeve 14 when the punch 12 is driven downward toward die 16 during a punching operation. Although other frame support may be used, the C-frame design of support 18 minimizes the size and footprint of the apparatus and minimizes vibration as well.

The integrated stripping sleeve 14 prevents motion of the porous substrate as punch 12 punches through substrate 28 and die 16, and then as punch 12 is retracted back through die 16 and substrate 28 after a piece is cut out of the substrate. The continuous punch control of apparatus 10 with a full stroke all the way through die 16 reduces the complexity of the apparatus and obviates the need for an ejector pin associated with previous punching systems.

The moving parts of apparatus 10 may be removed from apparatus 10 as a unit, by removing the pillar assembly from the c-frame support 18 along the punch axis. An embodiment of pillar 20 is shown in FIGS. 9A and 9B generally show the location set screw 32 and pin guide 35 of this example embodiment.

Once removed, any of the subcomponents of the unit may be replaced or interchanged. To access the punch 12, the stripping sleeve 14 may be removed and replaced by removing pins 52 from pin holes 35 and sliding the sleeve and spring 26 from counter bore 37 in pillar 20. The punch 12 may be removed and replaced by removing the engagement components, such as set screw 32 which passes through the pillar 20 into the punch. The common support design of apparatus 10 allows the various components of the apparatus to be readily interchanged in the field. The puncher may be interchanged, for example, to accommodate different punch sizes or when the punch head becomes worn. Sample pieces of porous substrates used to in biological sample testing systems are typically between 1 and 6 mm in diameter, which determine the size of die 16, punch head 34 and stripping sleeve head 36. However, the apparatus is not limited to such shapes or sizes and may be adapted for any suitably sized pieces to be cut out of the sample substrate.

Figure 3B:
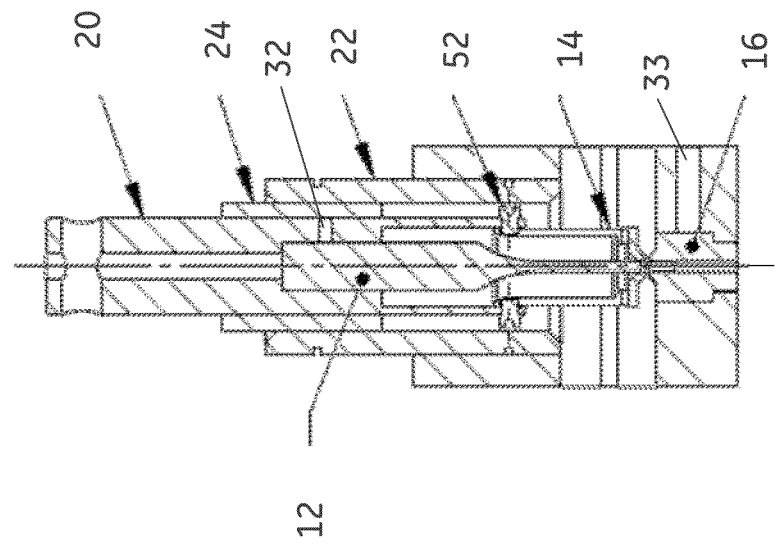
FIG. 3B is a cross-sectional view of the apparatus shown in FIG. 3A through line B-B.
Figure 3A:
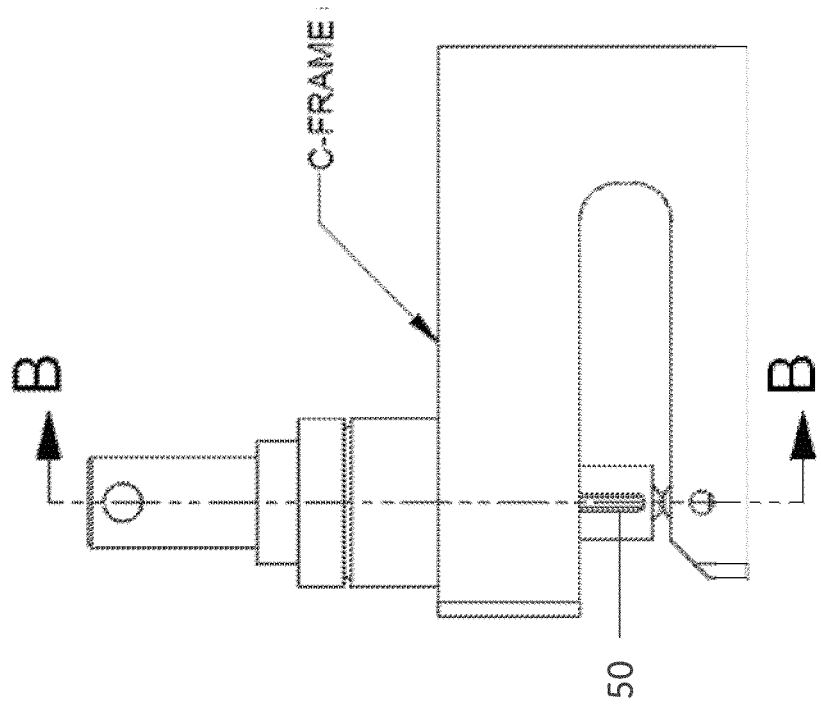
FIG. 3A is side view of the apparatus shown in FIG. 2A

Apparatus 10 is adapted to cut a sample piece, having a predetermined shape and an outer dimension, out of a porous substrate, such as FTA card 28. Punch 12 has a defined outer dimension at the head or distal end 34 of the punch that contacts the FTA card. The defined outer diameter of the punch head 34 substantially corresponds to the predetermined shape and outer dimension of the sample piece to be cut out of the card. The outer dimension is the largest dimension of the piece that will determine the size of the punch head and, in turn, the size of the die through which the punch head cuts and pushes the cut piece through and into a receptacle. For example, the outer dimension of the sample piece would be the diameter if the sample piece to be cut is a round disc. If the piece is intended to be cut as a square or rectangle, then the outer dimension would be the length and the width. Stripping sleeve 14 has a stripping head 36 that also substantially corresponds to the shape and outer dimension of the sample piece, although the stripping head is larger than both the punch head and the sample piece, to hold the porous substrate against a surface of die 16 of apparatus 10 as the die cuts out a piece of the substrate. Die 16 has an innermost dimension, such as an inner diameter, that is larger than the outermost dimension of the punch head. A fixture, such as C-frame support 18 holds the die in a fixed position relative to the puncher and stripping sleeve. The die or punch bushing may also be interchangeable by removing a setscrew 33, shown in FIG. 3B.

Figure 6:
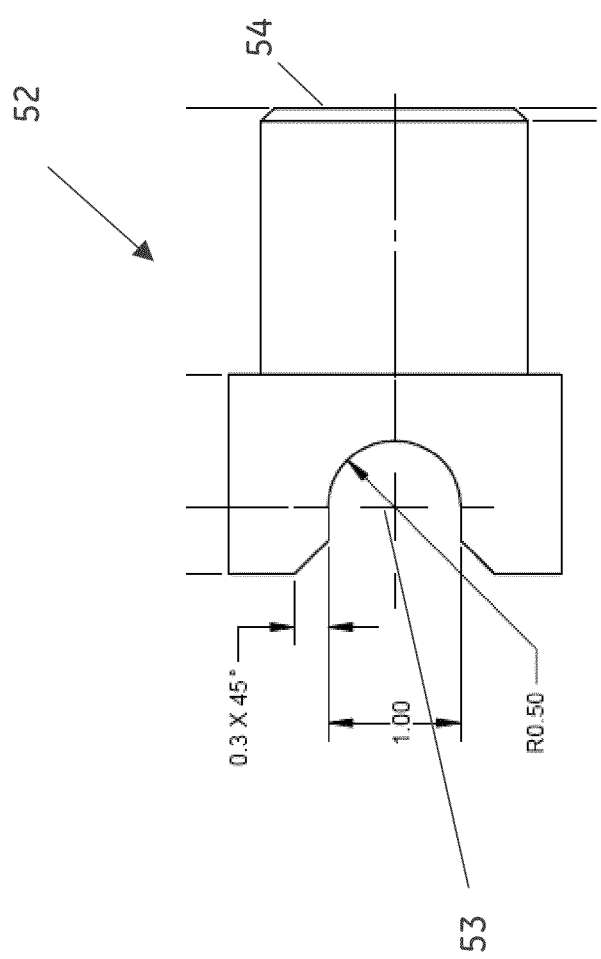
FIG. 6 is a side view of an embodiment of the slot guide for a stripping sleeve.

Stripping sleeve 14 comprises elongated slots or channels 50 through which guides, such as stripping sleeve pins 52 extend. Pins 52 are seated in the lower portion of pillar 20. A retaining ring or clip engages with pin 52 in the notch area 53 to hold the pins in place against the pillar 20. FIG. 6 shows an embodiment of stripping sleeve pin 52 having a head 54 that engages slot 50. Slots 50 are necessarily limited to an opening that completely perforates the wall of the stripping sleeve. For example, depending on the material the sleeve and the thickness of the wall of the sleeve, the slot could also be a channel or groove that does not perforate the inner surface of the sleeve.

In at least one embodiment, for example, apparatus 10, the pillar comprises a seat for the guide, and the stripping sleeve comprises one or more channels that engage the guides. In another embodiment, the sleeve comprises the seat for the guide and the pillar comprises the channels which engage the guides.

Figure 4B:
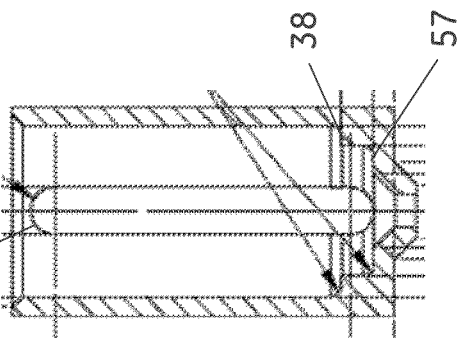
FIG. 4A is a side view of an embodiment of the stripping sleeve with the inner wall shown in phantom and FIG. 4B is a cross-sectional view of the stripping sleeve shown in FIG. 4A through line A-A.
Figure 4A:
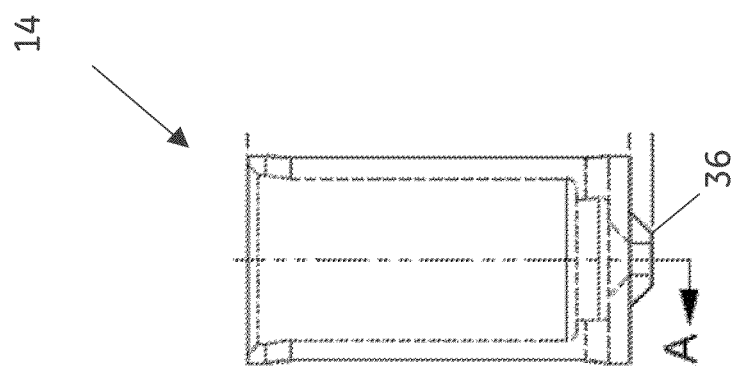

When in a resting mode, pins 52 are located at the upper end of slot 50. As stripping sleeve 14 is actuated by loaded spring 26, slots 50 together with pins 52 allow sleeve 14 to move in a vertical direction to an extent that is determined by the length of slot 50. The upper end 56 of slot 50 serves as a stop for pin 52 when at the punch is at rest. The lower end 57 serves as a hard stop for pin 52 but the pin should never limit the motion in the direction of the lower end 57 under normal operating conditions. When the sleeve 14 reaches the desired point at which sleeve head 36 is providing just enough pressure on FTA card 28 to hold it in place on support 18 without making an imprint in, or otherwise damaging, the FTA card 28 or a biological sample on the card. The end of the sleeve 36 should extend beyond the punch 12 such that the punch is recessed within the sleeve in the resting mode; in this way, the sleeve will maintain contact prior, during, and after the punch contacts the card 28.] In this embodiment, the length of slot 50 will generally be determined by the length of die 16 together with the thickness of card 28. Sleeve 14, as shown in FIGS. 4A and 4B has a sleeve head 36 that is substantially smaller that the upper inner diameter of sleeve 14, to accommodate punches for cutting relatively small pieces of porous substrates. The embodiment of the sleeve head shown in FIGS. 4A and 4B graduates from a larger diameter to a smaller diameter sleeve head in part by a series of stepped shoulders and a gradual tapered head. The loaded spring 26 of apparatus 10 is seated, and presses against, shoulder 38 during a punching operation. Another embodiment of a stripping sleeve is shown in FIGS. 5A and 5B. Stripping sleeve 60 has a sleeve head 64 having a diameter than is larger, than sleeve head 36 relative to the upper inner diameter of the sleeve, to accommodate punches for cutting relatively larger piece of porous substrates. Sleeve 60 also has shoulder 62 that similarly serves in part as a stop for a loaded spring.

The components of apparatus 10, such as pillar 20, hardliner 22, roller ball cage 24, punch 12 and die 16 should be made of materials that are suited to withstand a reasonable amount of use so as to reduce the amount of wear on the parts and the frequency of changing the components. Sleeve 14 may be made from a variety of materials such as aluminum, plastic and steel. Generally though, materials that are lighter in weight but which are still able to withstand repeated use, such as aluminum, may be more suitable that heavier materials, such as steel, to reduce the overall weight of the apparatus.

Figure 2B:
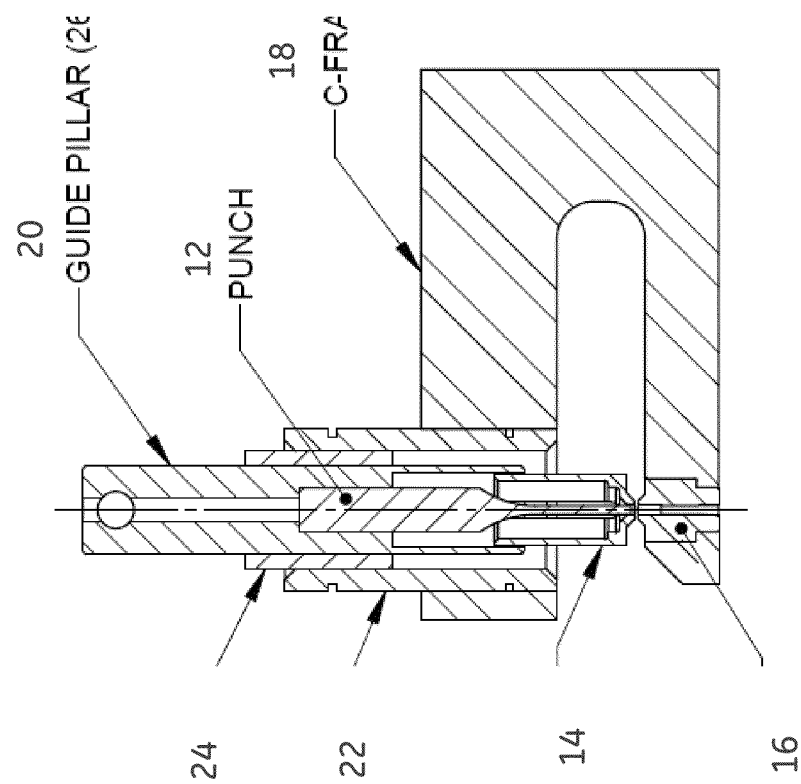
FIG. 2A is a front view of an embodiment of the apparatus of the invention and FIG. 2B is a cross-section view of the apparatus of FIG. 2A through line A-A.
Figure 2A:
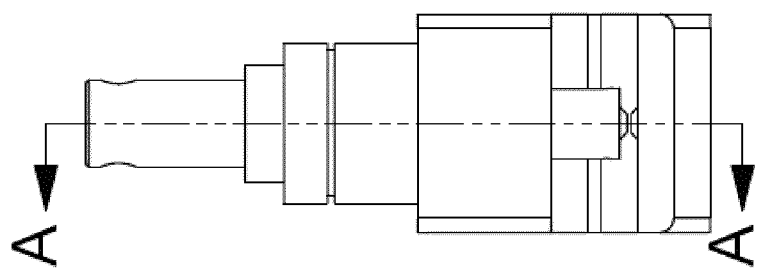
Figure 8:
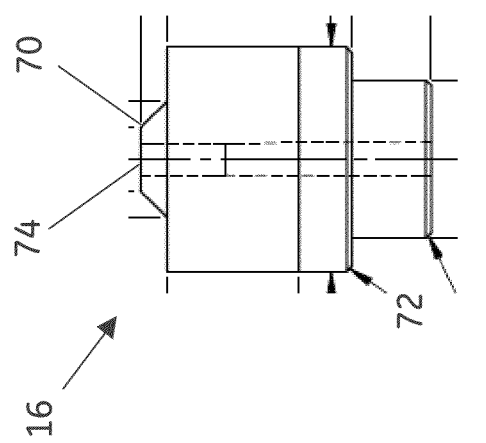
FIG. 8 is another embodiment of a punch bushing.

Die 16 may be a punching bushing as shown in FIGS. 1, 2 and 8. Punch bushing 16 has an inner bore 74 that is only slightly larger than the outer diameter of punch head 34. Bushing 16 has a tapered head 70 to accommodate small punch heads for cutting relatively small pieces of the porous substrate. Bushing 16 also has a shoulder 72 on which the bushing rests when seated on a corresponding shoulder of lower arm 42 of C-frame support 18. The bore of the die may gradually increase in diameter from the top entrance of the die to the bottom exit of the die.

Figure 7:
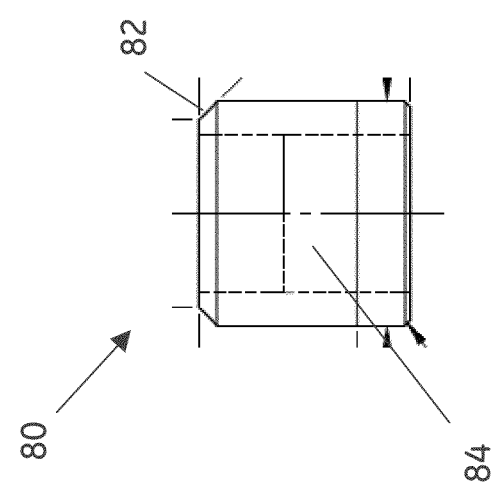
FIG. 7 is an embodiment of the punch bushing.

Another embodiment of a die or punch bushing is shown and referred to in FIG. 7 as bushing 80 which has a head 82 and inner bore 84 that are larger relative to the outside diameter of the bushing to accommodate larger punch heads for cutting relatively larger pieces of a porous substrate.

The punching method is illustrated in the example shown by the cross-sectionals views of FIGS. 10A-10C. The punch performs the blanking process by shearing the FTA substrate using a traditional punch and die approach. The punch head generally moves at high speed (e.g. 500 mm/sec) and pushes the substrate through the bottom die, creating a blank (sample disc) in the shape of the die. The clearance between the cylindrical punch and the cylindrical opening in the die is very tight (e.g. about 0.0002" or 5 μm) to ensure a high quality blank with little or no fraying.

The stripping sleeve that holds the FTA substrate in place during the punch and retraction motions. The stripping sleeve is a spring-loaded component that engages stripping sleeve pin and moves with the punch head. The stripping sleeve in this example has a pre-load of about 13N and is slotted to allow for relative motion with sleeve pin and punch. As the punch head and sleeve pin move downward towards the die, the loaded spring pushes against a shoulder of the sleeve. This action forces the sleeve downward until the sleeve head contacts the FTA substrate just before the punch, because, in this example, the punch is slightly recessed within the sleeve. In embodiments in which the FTA substrate positioned against the bottom die, the pre-load of the stripping sleeve is transferred to the FTA substrate. As the punch continues into and through the die, a blank (cut disc) is created and continues to be pushed through the die by the punch. During this portion of the operation, the stripping sleeve continues to push and hold the FTA substrate against a portion of the bottom die. The holding force reaches a peak at the max stroke of the punch head (e.g. approximately 22N). As the punch is retracted through the die, the edges of the substrate are in contact with the body of the punch and the friction applies an upward force on the substrate. The stripping sleeve applies a downward force on the substrate to prevent any motion of the substrate, so long as the force (ranging from peak force to preload force) is less than the upward force created by punch retraction. Because the punch is normally, in this example, slightly recessed in the stripping sleeve, the sleeve continues to apply a downward force until the punch is fully retracted from the substrate.

The component design and configuration also serves to provide positive sample control. The punch mechanism is configured so that the punched sample disc is unlikely to become stuck in an undesirable location. Lost samples increase the risk of cross contamination and may result in requiring a large number of samples being retaken. The positive sample control is implemented by ensuring that the stroke of the punch continues all the way through the die. If a receptacle is positioned directly under and in contact with the immediate underside of the bottom die, the location of the cut sample disc will be ensured after the punching operation.

The methods and systems of the invention may be used in conjunction (e.g. in-line) with analytical systems that analyze the samples and materials extracted from the samples on the porous substrates for many different purposes such as, but not limited to, immunoassays (e.g. to identify the presence or absence of a component), liquid chromatography with UV detection (e.g. to characterize and quantify components), liquid chromatography with mass spectrometry (e.g. to identify and/or quantify components), and polymerase chain reaction (PCR) for DNA analysis. The methods and systems may be adapted for high-throughput applications.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An apparatus for cutting a sample piece, having a shape and an outer dimension, out of a porous substrate, comprising:
    a puncher having an outermost dimension at a punch head;
    a stripping sleeve comprising one or more channels configured to receive one or more guides;
    a die having an innermost dimension that is larger than the outermost dimension of the punch head; and
    a c-frame fixture that holds the die in a fixed position relative to the puncher and stripping sleeve, wherein the punch head is configured to pass through the die and a bottom of the c-frame fixture in a fully extended position;
    a support coupled to the c-frame fixture;
    a roller ball cage positioned coaxially within the c-frame fixture;
    a pillar positioned coaxially within the roller ball cage and positioned about the stripping sleeve;
    one or more guides coupled to the pillar and corresponding to the one or more channels wherein the one or more guides are configured to change position within the one or more channels when the stripping sleeve moves relative to the pillar and wherein the one or more guides comprise a head portion that is received in the one or more channels and a notch portion that engages with a retaining element to retain the one or more guides on the pillar, wherein the notch portion is wider than the head portion such that the notch portion forms a flange extending from the head portion; and
    a spring positioned on an interior of the pillar and the stripping sleeve and about the puncher.

2. The apparatus of claim 1, wherein the stripping sleeve has a stripping head that corresponds to the shape and outer dimension of the punch head.

3. The apparatus of claim 1, wherein the stripping sleeve is spring loaded.

4. The apparatus of claim 1, wherein the punch head has a length and the one or more channels have a length that corresponds to the punch head length.

5. The apparatus of claim 1, wherein the puncher is coaxially located within the stripping sleeve and the puncher has a path axis along which the puncher moves within the stripping sleeve.

6. The apparatus of claim 5, wherein the stripping sleeve is spring-loaded and has a shoulder against which the spring presses.

7. The apparatus of claim 6, wherein the spring is coaxially located between an inner surface of the sleeve and an outer surface of the puncher.

8. The apparatus of claim 1, wherein the pillar and puncher are removeable from the fixture by disengaging the engaging components.

9. The apparatus of claim 8, wherein at least one of the engaging components comprises a set screw.

10. The apparatus of claim 1, wherein the spring is in direct contact with the puncher within the pillar, and wherein there is a gap between the spring and the puncher within the stripping sleeve.

* * * * *